United States Patent
Chen et al.

(10) Patent No.: US 10,836,823 B2
(45) Date of Patent: *Nov. 17, 2020

(54) DSG2 MONOCLONAL ANTIBODY AND THE APPLICATIONS THEREOF

(71) Applicant: Asclepiumm Taiwan Co., Ltd, New Taipei (TW)

(72) Inventors: Min-che Chen, New Taipei (TW); Po-hao Chang, New Taipei (TW); Ya-chuan Liu, New Taipei (TW)

(73) Assignee: ASCLEPIUMM TAIWAN CO., LTD., New Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 16/307,441

(22) PCT Filed: Jun. 6, 2016

(86) PCT No.: PCT/CN2016/085001
§ 371 (c)(1),
(2) Date: Dec. 5, 2018

(87) PCT Pub. No.: WO2017/210844
PCT Pub. Date: Dec. 14, 2017

(65) Prior Publication Data
US 2019/0300604 A1    Oct. 3, 2019

(51) Int. Cl.
| C07K 16/00 | (2006.01) |
| C07K 16/46 | (2006.01) |
| C07K 16/28 | (2006.01) |
| A61P 35/04 | (2006.01) |
| A61K 39/395 | (2006.01) |
| C12N 15/85 | (2006.01) |
| A61P 35/00 | (2006.01) |

(52) U.S. Cl.
CPC ........ *C07K 16/28* (2013.01); *A61K 39/39558* (2013.01); *A61P 35/00* (2018.01); *A61P 35/04* (2018.01); *C12N 15/85* (2013.01)

(58) Field of Classification Search
None
See application file for complete search history.

(56) References Cited

U.S. PATENT DOCUMENTS

| 8,168,180 B2 * | 5/2012 | Neufeld ................ C07K 16/30 424/130.1 |
| 9,376,492 B2 * | 6/2016 | Chen ................ A61K 39/39533 |
| 2004/0229811 A1 | 11/2004 | Blaschuk et al. |
| 2012/0276082 A1 | 11/2012 | Chen |
| 2016/0097096 A1 | 4/2016 | Min et al. |

FOREIGN PATENT DOCUMENTS

| WO | 1999057149 A2 | 11/1999 |
| WO | 2011036440 A1 | 3/2011 |
| WO | 2014/052322 A1 | 4/2014 |

OTHER PUBLICATIONS

Brown et al. Tolerance of single, but not multiple, amino acid replacements in antibody VH CDR 2: a means of minimizing B cell wastage from somatic hypermutation? J. Immuno. May 1996, 3285-91. (Year: 1996).*
Vajdos et al. Comprehensive functional maps of the antigen-binding site of an anti-ErbB2 antibody obtained with shotgun scanning mutagenesis. J. Mol. Biol., Jul. 5, 2002, 320(2):415-28. (Year: 2002).*
Paul, Fundamental Immunology, 3rd Edition, 1993, pp. 292-295. (Year: 1993).*
Rudikoff et al Single amino acid substitution altering antigen-binding specificity. Proc Natl Acad Sci U S A. Mar. 1982;79(6):1979-83 (Year: 1982).*
International Search Report dated Dec. 14, 2017 in corresponding International Application No. PCT/CN2016/085001.
Chothia C & Lesk AM "Canonical structures for the hypervariable regions of immunoglobulins." (1987) J. Mol. Biol. 196: 901-917.
Lefranc MP et al., (1999) "IMGT, the international ImMunoGeneTics database." Nucleic Acids Res. 27(1): 209-212.
Lefranc MP (2001) "IMGT, the international ImMunoGeneTics database." Nucleic Acids Res. 29(1): 207-209.
Lefranc MP (2003) "IMGT, the international ImMunoGeneTics database." Nucleic Acids Res. 31(1): 307-310.
Rees, Anthony R., et al. "Antibody combining sites: structure and prediction." in Sternberg, M.J.E. (ed.), Protein Structure Prediction, 1st ed., (1996): Oxford University Press, pp. 141-172.
Ruiz M et al., (2000) "IMGT, the international ImMunoGeneTics database." Nucleic Acids Res. 28(1): 219-221.
Orlandi R et al., (1989) "Cloning immunoglobulin variable domains for expression by the polymerase chain reaction." Proc. Natl. Acad. Sci., USA, 86: 3833-3837.
Leung, Shui-on, et al. "Construction and characterization of a humanized, internalizing, B-cell (CD22)-specific, leukemia/lymphoma antibody, LL2." Molecular immunology 32.17-18 (1995): 1413-1427.
Leung, S. O., et al. "Chimerization of LL2, a rapidly internalizing antibody specific for B cell lymphoma." Hybridoma 13.6 (1994): 469-476.
Jones, Peter T., et al. "Replacing the complementarity-determining regions in a human antibody with those from a mouse." Nature 321.6069 (1986): 522-525.
Riechmann, Lutz, et al. "Reshaping human antibodies for therapy." Nature 332.6162 (1988): 323.
Verhoeyen, Martine, Cesar Milstein, and Greg Winter. "Reshaping human antibodies: grafting an antilysozyme activity." Science 239. 4847 (1988): 1534-1536.
Carter, Paul, et al. "Humanization of an anti-p185HER2 antibody for human cancer therapy." Proceedings of the National Academy of Sciences 89.10 (1992): 4285-4289.

(Continued)

*Primary Examiner* — Maher M Haddad
(74) *Attorney, Agent, or Firm* — Duane Morris LLP (57) ABSTRACT

The invention provides antibodies against the antigen containing the Dsg2 extracellular domain 2. Also provided is the method of using the antibodies in treatment or prevention of a cancer.

6 Claims, 7 Drawing Sheets

Specification includes a Sequence Listing.

(56) References Cited

OTHER PUBLICATIONS

Sandhu, Jasbir Singh. "Protein engineering of antibodies." Critical reviews in biotechnology 12.5-6 (1992): 437-462.
Tempest, Philip R., et al. "Reshaping a human monoclonal antibody to inhibit human respiratory syncytial virus infection in vivo." Bio/Technology 9.3 (1991): 266-271.
Singer, Irwin I., et al. "Optimal humanization of 1B4, an anti-CD18 murine monoclonal antibody, is achieved by correct choice of human V-region framework sequences." The Journal of Immunology 150.7 (1993): 2844-2857.
Extended European Search Report in EP Application No. 16904297.5, dated Jan. 2, 2020, in 8 pages.
Saaber, Friederike, et al. "Expression of desmogleins 1-3 and their clinical impacts on human lung cancer." Pathology—Research and Practice 211.3 (2015): 208-213.
Davies, E., et al. "The role of desmoglein 2 and E-cadherin in the invasion and motility of human breast cancer cells." International Journal of Oncology 11.2 (1997): 415-419.
Office Action in Japan Counterpart Application No. 2019-516036, dated Feb. 20, 2020, in 9 pages; English translation provided.
Schäfer, Stephan, et al. "Immunological identification and characterization of the desmosomal cadherin Dsg2 in coupled and uncoupled epithelial cells and in human tissues." Differentiation 60.2 (1996): 99-108.
Brennan, Donna, et al. "Increased expression of Dsg2 in malignant skin carcinomas: A tissue-microarray based study." Cell Adhesion & Migration 3.2 (2009): 148-154.
Kamekura, Ryuta, et al. "Inflammation-induced desmoglein-2 ectodomain shedding compromises the mucosal barrier." Molecular Biology of the Cell 26.18 (2015): 3165-3177.
Giusti, Betti, et al. "A model of anti-angiogenesis: differential transcriptosome profiling of microvascular endothelial cells from diffuse systemic sclerosis patients." Arthritis Research & Therapy 8.4 (2006): R115, 17 pages.

\* cited by examiner

3D4 VH (Variable Region of Heavy Chain)
QIQLVQSGPELKKPGETVKISCKAS<u>GYTFTNYG</u>MNWVRQAPGKA
                        CDR1
LKWMVW<u>MNTNTGES</u>IYAEEFKGRFVFSLDTSASTAYLQINNLNNE
        CDR2
DTATYFC<u>ARYWDTY</u>WGQGTTLTVSS
       CDR3

3D4 VL (Variable Region of Light Chain)
DIKMTQSPSSMYASLGERVTITCKAS<u>QDINSY</u>LSWFQQKPGKSPKTLIY
                             CDR1
<u>RANRLVD</u>GVPSRFSGSGSGQDFSLTISSLEYEDMGIYYC<u>LQYDEFPYTF</u>
CDR2                                                        CDR3
GGGTKLEIK

13D3 VH (Variable Region of Heavy Chain)
QVQLQQPGAELVKPGASVKLSCKAS<u>GYTFTSYY</u>MYWVKQRPGQ
                        CDR1
GLEWIGG<u>INPNNGGT</u>NFNEKFKSKATLTVDKSSSTAYMQLRSLTS
        CDR2
EDSAVYYC<u>IRGSGYGN</u>WGQGTLVTVSA
        CDR3

13D3 VL (Variable Region of Light Chain)
DIKMTQSPSSMYASLGERVTITCKAS<u>QDINGY</u>LSWFQQKPGKSPKTLIY
                              CDR1
<u>RANRLVD</u>GVPSRFSGSGSGQDYSLTISSLEYEDMGIYYC<u>LQYDEFPYTF</u>
CDR2                                                    CDR3

DSG2 MONOCLONAL ANTIBODY AND THE APPLICATIONS THEREOF

CROSS-REFERENCE TO RELATED APPLICATION

This application is a § 371 national stage entry of International Application No. PCT/CN2016/085001, filed Jun. 6, 2016, the entire contents of which are incorporated herein by reference.

FIELD OF THE INVENTION

The present invention relates to an antibody for cancer treatment. Particularly, the present invention relates to Dsg2 monoclonal antibodies and uses in treatment of cancer.

BACKGROUND OF THE INVENTION

Desmosomes are one of the principal types of cell-cell adhesion junction between epithelial, myocardial and other tissues. Such desmosomes contain transmembrane glycoproteins called desmosomal cadherin, desmocollin (Dsc) and desmoglein (Dsg). Each occurs as at least three distinct genetic isoforms that show tissue-specific expression patterns.

Dsg2 are ubiquitously expressed in all tissues that form desmosomes. The extracellular domains of Dsg2 contain four cadherin repeat domains (EC1-4), each about 110 amino acids each in length. The extracellular repeat domain EC1 contains cell adhesion recognition (CAR) sites, which provide cell-cell adhesion. Therefore, Dsg2 has been identified to be a transmembrane cell adhesion molecule. Additionally, recent studies show that Dsg2 is not just a simple cell-cell adhesion molecule. Dsg2 is involved in promotion of angiogenesis, signalling of apoptosis, and is a substrate for MMPs.

Dsg2 has an important role in regulating EMT. They have shown that: (1) triggering EMT using hepatocyte growth factor/scattering factor (HGF/SF) shows that most of the desmosomal adhesion components are down-regulated, except Dsg2. (2) epithelial cells transfected with Dsg2 exhibit a mesenchymal-like morphology and show greater migration and invasion abilities under treatment by HGF/SF. (3) antibodies against EC2 domain of Dsg2 significantly block HGF/SF-induced EMT in vitro. Furthermore, the inventors have determined that antibodies to the EC2 domain of Dsg2 inhibit invasion of cancer cells, including MCF7 human breast cancer cells, LNCaP human prostate cancer cells, and KM12 human colon cancer cells. While not wishing to be bound to any particular theory, they propose that Dsg2 can function in the cell to promote EMT. US 20040229811 teaches cancer treatment by inhibiting adhesion of dsc- and/or dsg-expressing cells in a mammal. WO 99/57149 suggests that cell adhesion recognition (CAR) sites derived from the EC2 domain of Dsg2 can be used as modulating agents for treating cancer and/or inhibiting metastasis. US 20120276082 discloses an antagonist of Dsg2 wherein said antagonist modulates the function of the EC2 domain of Dsg2.

It has been implied that Dsg2 is involved in human diseases such as cancer, which Dsg2 is highly expressed in several epithelial-derived malignancies including basal cell carcinomas (BCC), squamous cell carcinomas (SCC), gastric cancer, melanoma, metastatic prostate cancer and bladder cancer. However, there remains a need in the art for antibodies targeting against Dsg2 that can be used in preventing or treating cancer.

SUMMARY OF THE INVENTION

The present invention relates to Dsg2 monoclonal antibodies and uses in treatment of cancer.

The invention provides an isolated monoclonal antibody, which specifically binds to Dsg2. In some embodiments, the antibody is a chimeric antibody, a CDR-grafted antibody, or a humanized antibody.

The invention also provides a Dsg2 monoclonal antibody or an antigen-binding portion thereof, comprising at least one of a heavy chain complementarity determining region 1 (H-CDR1) comprising the amino acid residue of SEQ ID NO: 1 or 2, or a variant having amino acid sequence with at least 80%, 85%, 90%, 91%, 92%, 93%, 94%, 95%, 96%, 97%, 98% or 99% identity to any of SEQ ID NOs: 1 to 2; a heavy chain CDR2 (H-CDR2) comprising the amino acid residue of SEQ ID NO: 3 or 4, or a variant having amino acid sequence with at least 80%, 85%, 90%, 91%, 92%, 93%, 94%, 95%, 96%, 97%, 98% or 99% identity to any of SEQ ID NOs: 3 to 4; and a heavy chain CDR3 (H-CDR3) comprising the amino acid residue of SEQ ID NO: 5 or 6, or a variant having amino acid sequence with at least 80%, 85%, 90%, 91%, 92%, 93%, 94%, 95%, 96%, 97%, 98% or 99% identity to any of SEQ ID NOs: 5 and 6; and at least one of a light chain CDR1 (L-CDR1) comprising the amino acid residue of SEQ ID NO: 7 or 8, or a variant having amino acid sequence with at least 80%, 85%, 90%, 91%, 92%, 93%, 94%, 95%, 96%, 97%, 98% or 99% identity to any of SEQ ID NOs: 7 and 8; a light chain CDR2 (L-CDR2) comprising the amino acid residue of SEQ ID NO: 9, or a variant having amino acid sequence with at least 80%, 85%, 90%, 91%, 92%, 93%, 94%, 95%, 96%, 97%, 98% or 99% identity to SEQ ID NO: 9; and a light chain CDR3 (L-CDR3) comprising the amino acid residue SEQ ID NO: 10, or a variant having amino acid sequence with at least 80%, 85%, 90%, 91%, 92%, 93%, 94%, 95%, 96%, 97%, 98% or 99% identity to SEQ ID NO: 10; such that said isolated antibody or antigen-binding portion thereof binds to Dsg2.

In some embodiment, the present invention provides a Dsg2 monoclonal antibody or an antigen-binding portion thereof, comprising a) H-CDR1H of SEQ ID NO:1, H-DR2H of SEQ ID NO:3, H-CDR3H of SEQ ID NO:5 and L-CDR1 of SEQ ID NO:7, L-CDR2 of SEQ ID NO:9, L-CDR3 of SEQ ID NO:10, or b) H-CDR1H of SEQ ID NO:2, H-DR2H of SEQ ID NO:4, H-CDR3H of SEQ ID NO:6 and L-CDR1 of SEQ ID NO:8, L-CDR2 of SEQ ID NO:9, L-CDR3 of SEQ ID NO:10. In another embodiment, the present invention provides a Dsg2 monoclonal antibody or an antigen-binding portion thereof, comprising H-CDR1H of SEQ ID NO:2, H-CDR2H of SEQ ID NO:4, H-CDR3H of SEQ ID NO:6 and L-CDR1 of SEQ ID NO:8, L-CDR2 of SEQ ID NO:9, L-CDR3 of SEQ ID NO:10.

In one embodiment, the Dsg2 monoclonal antibody or an antigen-binding portion thereof, comprising a light chain variable region amino acid sequence of SEQ ID NO:11 or 12. In another embodiment the Dsg2 monoclonal antibody or an antigen-binding portion thereof, comprising a heavy chain variable region amino acid sequence of SEQ ID NO:13 or 14. In a further embodiment, the Dsg2 monoclonal antibody or an antigen-binding portion thereof, comprising a light chain variable region amino acid sequence of SEQ ID NO:11 and a heavy chain variable region amino acid sequence of SEQ ID NO:13 (3D4). In another further embodiment, the Dsg2 monoclonal antibody or an antigen-binding portion thereof, comprising a light chain variable region amino acid sequence of SEQ ID NO:12 and a heavy chain variable region amino acid sequence of SEQ ID NO:14 (13D3).

The invention also provides a pharmaceutical composition comprising Dsg2 monoclonal antibody or an antigen-binding portion thereof of the invention and a pharmaceutically acceptable carrier or excipient.

The invention further provides a method for treating angiogenesis, comprising administering a monoclonal antibody of the invention to a subject. Further, the invention provides a method for treating cancer and/or inhibiting invasion and metastasis, comprising administering a monoclonal antibody of the invention to a subject. In one embodiment, the method can reduce EMT and associated invasion and metastatic potential of cancerous cells. Preferably, the cancer is kidney cancer, melanoma, lung cancer, esophageal cancer, cervical cancer, breast cancer or pancreatic cancer.

BRIEF DESCRIPTION OF THE DRAWING

FIG. 2 A to D shows Dsg2 knockdown studies by flow cytometric analysis and Western blotting show that 3D4 and 13D3 with specifically binding activities to Dsg2. A: flow cytometric analysis of 3D4; B: Western blotting of 3D4; C: flow cytometric analysis of 13D3; D: Western blotting of 13D3.

FIG. 3 A to D shows flow cytometric analysis and Western blotting studies of Dsg2 overexpression cells show that 3D4 and 13D3 can specifically bind to Dsg2. A: flow cytometric analysis of 3D4; B: Western blotting of 3D4; C: flow cytometric analysis of 13D3; D: Western blotting of 13D3.

DETAILED DESCRIPTION OF THE INVENTION

The invention found that antibodies against Dsg2 provide advantageous efficacy in treatment or prevention of a cancer.

In the description that follows, a number of terms are used and the following definitions are provided to facilitate understanding of the claimed subject matter. Terms that are not expressly defined herein are used in accordance with their plain and ordinary meanings.

Unless otherwise specified, a or an means "one or more."

As used herein, the term "epitope" refers to the site on the antigen to which an antibody binds. The term "antigen" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen.

The term "antibody" as referred to herein includes whole antibodies and any antigen binding fragments or single chains thereof. An "antibody" refers to a glycoprotein comprising at least two heavy (H) chains and two light (L) chains inter-connected by disulfide bonds, or an antigen binding fragment thereof. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR) with are hypervariable in sequence and/or involved in antigen recognition and/or usually form structurally defined loops, interspersed with regions that are more conserved, termed framework regions (FR or FW). Each VH and VL is composed of three CDRs and four FWs, arranged from amino-terminus to carboxy-terminus in the following order: FW1, CDR1, FW2, CDR2, FW3, CDR3, FW4. The amino acid sequences of FW1, FW2, FW3, and FW4 all together constitute the "non-CDR region" or "non-extended CDR region" of VH or VL as referred to herein.

A number of CDR definitions are in use and are encompassed herein. For example, the Kabat definition is based on sequence variability and is the most commonly used (Kabat E A et al., supra). Chothia refers instead to the location of the structural loops (Chothia C & Lesk A M (1987) J. Mol. Biol. 196: 901-917). The AbM definition is a compromise between the Kabat and the Chothia definitions and is used by Oxford Molecular's AbM antibody modelling software (Protein Structure Prediction. Oxford University Press, Oxford, 141-172). The definition of the CDR by IMGT, the international ImMunoGeneTics database (http://imgt.cines.fr) is a high quality integrated information system specializing in immunoglobulins (IG), T cell receptors (TR) and major histocompatibility complex (MHC) of human and other vertebrates. (Lefranc M P et al., (1991) Nucleic Acids Res. 27(1): 209-12; Ruiz M et al., (2000) Nucleic Acids Res. 28(1): 219-21; Lefranc M P (2001) Nucleic Acids Res. 29(1): 207-9; Lefranc M P (2003)).

The term "murine antibody" as used herein includes antibodies in which the variable region sequences and the constant region sequences are derived from a mouse.

As used herein, the term "chimeric antibody" refers to a recombinant protein that contains the variable domains of both the heavy and light antibody chains, including the complementarity determining regions (CDRs) of an antibody derived from one species, preferably a rodent antibody or a chicken antibody, more preferably a murine antibody, while the constant domains of the antibody molecule are derived from those of a human antibody.

As used herein, the term "Fv" is a minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

As used herein, the term "diagnostic" or "diagnosed" means identifying the presence or nature of a pathologic condition.

As used herein, the terms "treatment," "treating," and the like, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

As interchangeably used herein, the terms "individual," "subject," "host," and "patient," refer to a mammal, including, but not limited to, murines (rats, mice), non-human primates, humans, canines, felines, ungulates (e.g., equines, bovines, ovines, porcines, caprines), etc.

As used herein, the term "therapeutically effective amount" or "efficacious amount" refers to the amount of a subject Dsg2 monoclonal antibody that, when administered to a mammal or other subject for treating a disease, is sufficient to effect such treatment for the disease.

The present invention relates to Dsg2 monoclonal antibodies. Particularly, the Dsg2 is Dsg2 extracellular domain 2

In one aspect, the present invention provides a Dsg2 monoclonal antibody or an antigen-binding portion thereof, comprising at least one of a heavy chain complementarity determining region 1 (H-CDR1) comprising the amino acid residue of SEQ ID NO: 1 or 2, or a variant having amino acid sequence with at least 80%, 85%, 90%, 91%, 92%, 93%, 94%, 95%, 96%, 97%, 98% or 99% identity to any of SEQ ID NOs: 1 to 2; a heavy chain CDR2 (H-CDR2) comprising the amino acid residue of SEQ ID NO: 3 or 4, or a variant having amino acid sequence with at least 80%, 85%, 90%, 91%, 92%, 93%, 94%, 95%, 96%, 97%, 98% or 99% identity to any of SEQ ID NOs: 3 to 4; and a heavy chain CDR3 (H-CDR3) comprising the amino acid residue of SEQ ID NO: 5 or 6, or a variant having amino acid sequence with at least 80%, 85%, 90%, 91%, 92%, 93%, 94%, 95%, 96%, 97%, 98% or 99% identity to any of SEQ ID NOs: 5 and 6; and at least one of a light chain CDR1 (L-CDR1) comprising the amino acid residue of SEQ ID NO: 7 or 8, or a variant having amino acid sequence with at least 80%, 85%, 90%, 91%, 92%, 93%, 94%, 95%, 96%, 97%, 98% or 99% identity to any of SEQ ID NOs: 7 and 8; a light chain CDR2 (L-CDR2) comprising the amino acid residue of SEQ ID NO: 9, or a variant having amino acid sequence with at least 80%, 85%, 90%, 91%, 92%, 93%, 94%, 95%, 96%, 97%, 98% or 99% identity to SEQ ID NO: 9; and a light chain CDR3 (L-CDR3) comprising the amino acid residue SEQ ID NO: 10, or a variant having amino acid sequence with at least 80%, 85%, 90%, 91%, 92%, 93%, 94%, 95%, 96%, 97%, 98% or 99% identity to SEQ ID NO: 10; such that said isolated antibody or antigen-binding portion thereof binds to Dsg2. Preferably, the sequence identity as mentioned above is at least 81%, 82%, 83%, 84%, 85%, 86%, 87%, 88%, 89%, 90%, 91%, 91%, 92%, 93%, 94%, 95%, 96%, 97%, 98% or 99%.

The amino acid sequences of the complementarity determining regions (CDRs) in heavy chains and light chains are listed below respectively. The CDRs are numbered according to IMGT numbering system.

| CDRs of Heavy Chain | | |
|---|---|---|
| H-CDR1 | H-CDR2 | H-CDR3 |
| GYTFTNYG (SEQ ID NO: 1) | MNTNTGES (SEQ ID NO: 3) | ARYWDTY (SEQ ID NO: 5) |
| GYTFTSYY (SEQ ID NO: 2) | INPNNGGT (SEQ ID NO: 4) | IRGSGYGN (SEQ ID NO: 6) |

| CDRs of Light Chain | | |
|---|---|---|
| L-CDR1 | L-CDR2 | L-CDR3 |
| QDINSY (SEQ ID NO: 7) | RAN (SEQ ID NO: 9) | LQYDEFPYT (SEQ ID NO: 10) |
| QDINGY (SEQ ID NO: 8) | | |

In some embodiments, the antibody is a chimeric antibody, a CDR-grafted antibody, or a humanized antibody.

In some embodiment, the present invention provides a Dsg2 monoclonal antibody or an antigen-binding portion thereof, comprising a) H-CDR1H of SEQ ID NO:1, H-DR2H of SEQ ID NO:3, H-CDR3H of SEQ ID NO:5 and L-CDR1 of SEQ ID NO:7, L-CDR2 of SEQ ID NO:9, L-CDR3 of SEQ ID NO:10, or b) H-CDR1H of SEQ ID NO:2, H-DR2H of SEQ ID NO:4, H-CDR3H of SEQ ID NO:6 and L-CDR1 of SEQ ID NO:8, L-CDR2 of SEQ ID NO:9, L-CDR3 of SEQ ID NO:10. In a further embodiment, the present invention provides a Dsg2 monoclonal antibody or an antigen-binding portion thereof, comprising a) H-CDR1H of SEQ ID NO:1, H-DR2H of SEQ ID NO:3, H-CDR3H of SEQ ID NO:5 and L-CDR1 of SEQ ID NO:7, L-CDR2 of SEQ ID NO:9, L-CDR3 of SEQ ID NO:10. In another embodiment, the present invention provides a Dsg2 monoclonal antibody or an antigen-binding portion thereof, comprising H-CDR1H of SEQ ID NO: H-DR2H of SEQ ID NO:4, H-CDR3H of SEQ ID NO:6 and L-CDR1 of SEQ ID NO:8, L-CDR2 of SEQ ID NO:9, L-CDR3 of SEQ ID NO:10.

In one embodiment, the Dsg2 monoclonal antibody or an antigen-binding portion thereof, comprising a light chain variable region amino acid sequence of SEQ ID NO:11 or 12. In another embodiment the Dsg2 monoclonal antibody or an antigen-binding portion thereof, comprising a heavy chain variable region amino acid sequence of SEQ ID NO:13 or 14.

3D4 VL (Variable Region of Light Chain)
(SEQ ID NO: 11)
DIKMTQSPSSMYASLGERVTITCKAS<u>QDINSY</u>LSWFQQKPGKSPKTLI
                                          CDR1
Y<u>RAN</u>RLVDGVPSRFSGSGSGQDFSLTISSLEYEDMGIYYC<u>LQYDEFPY</u>
 CDR2                                                CDR3
<u>T</u>FGGGTKLEIK 13D3 VL (Variable Region of Light Chain)
(SEQ ID NO:12)
DIKMTQSPSSMYASLGERVTITCKAS<u>QDINGY</u>LSWFQQKPGKSPKTLI
                                          CDR1
Y<u>RAN</u>RLVDGVPSRFSGSGSGQDYSLTISSLEYEDMGIYYC<u>LQYDEFPY</u>
 CDR2                                               CDR3
<u>T</u>FGGGTKLEIK 3D4 VH (Variable Region of Heavy Chain)
(SEQ ID NO:13)
QIQLVQSGPELKKPGETVKISCKAS<u>GYTFTNYG</u>MNWVRQAPGKALKWM
                                       CDR1
VW<u>MNTNTGES</u>IYAEEFKGRFVFSLDTSASTAYLQINNLNNEDTATYFC -continued

```
        CDR2
ARYWDTYWGQGTTLTVSS
        CDR2

13D3 VH (Variable Region of Heavy Chain)
                                   (SEQ ID NO:14)
QVQLQQPGAELVKPGASVKLSCKASGYTFTSYYMYWVKQRPGQGLEWI
                         CDR1
GGINPNNGGTNFNEKFKSKATLTVDKSSSTAYMQLRSLTSEDSAVYYC
    CDR2
IRGSGYGNWGQGTLVTVSA
    CDR3
```

In one embodiment, the Dsg2 monoclonal antibody or an antigen-binding portion thereof, comprising a light chain variable region amino acid sequence of SEQ ID NO:11 or 12; and a heavy chain variable region amino acid sequence of SEQ ID NO:13 or 14. In a further embodiment, the Dsg2 monoclonal antibody or an antigen-binding portion thereof, comprising a light chain variable region amino acid sequence of SEQ ID NO:11 and a heavy chain variable region amino acid sequence of SEQ ID NO:13 (3D4). In another further embodiment, the Dsg2 monoclonal antibody or an antigen-binding portion thereof, comprising a light chain variable region amino acid sequence of SEQ ID NO:12 and a heavy chain variable region amino acid sequence of SEQ ID NO:14 (13D3).

In another aspect, the present disclosure also provides an antibody or fragment thereof that binds to Dsg2, wherein at least one of the heavy chain CDRs and/or at least one of the light chain CDRs comprises at least one amino acid modification. Site-directed mutagenesis or PCR-mediated mutagenesis can be performed to introduce the modification(s) and the effect on antibody binding, or other functional property of interest, can be evaluated in in vitro or in vivo assays. Preferably conservative modifications are introduced. The modification(s) may be amino acid substitutions, additions or deletions, but are preferably substitutions. Typically, no more than five, preferably no more than four, more preferably no more than three, even more preferably no more than two, most preferably no more than one amino acid modifications are performed within a CDR region.

In certain embodiments, framework sequences can be used to engineer variable regions to produce variant antibodies. Variant antibodies of the invention include those in which modifications have been made to framework residues within VH and/or VK, e.g. to improve the properties of the antibody. Typically, such framework modifications are made to decrease the immunogenicity of the antibody. For example, one approach is to "backmutate" one or more framework residues to the corresponding murine sequence or to "backmutate" one or more framework residues to a corresponding germline sequence.

While particularly preferred methods of generating monoclonal antibodies of the invention are described in detail herein, a variety of other techniques, including conventional monoclonal antibody methodology e.g., the standard somatic cell hybridization technique also can be used. Although somatic cell hybridization procedures are preferred, other techniques for producing monoclonal antibody can be employed.

The preferred animal system for preparing hybridomas is the murine system. Hybridoma production in murine systems is a well-established procedure. Immunization protocols and techniques for isolation of immunized splenocytes for fusion are well known in the art. Fusion partners (e.g., murine myeloma cells) and fusion procedures are also well known. Briefly, monoclonal antibodies can be obtained by injecting mice or chicken with a composition comprising an antigen, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

Various techniques, such as production of chimeric or humanized antibodies, may involve procedures of antibody cloning and construction. The antigen-binding variable light chain and variable heavy chain sequences for an antibody of interest may be obtained by a variety of molecular cloning procedures, such as RT-PCR, 5'-RACE, and cDNA library screening. The variable heavy or light chain sequence genes of an antibody from a cell that expresses a murine antibody can be cloned by PCR amplification and sequenced. To confirm their authenticity, the cloned VL and VH genes can be expressed in cell culture as a chimeric antibody as described by Orlandi et al., (Proc. Natl. Acad. Sci., USA, 86: 3833 (1989)). Based on the variable heavy or light chain gene sequences, a humanized antibody can then be designed and constructed as described by Leung et al. (Mol. Immunol., 32: 1413 (1995)).

A chimeric antibody is a recombinant protein in which the variable regions of a human antibody have been replaced by the variable regions of, for example, a mouse antibody, including the complementarity-determining regions (CDRs) of the mouse antibody. Chimeric antibodies exhibit decreased immunogenicity and increased stability when administered to a subject. Methods for constructing chimeric antibodies are well known in the art (e.g., Leung et al., 1994, Hybridoma 13:469).

A chimeric monoclonal antibody may be humanized by transferring the mouse CDRs from the heavy and light variable chains of the mouse immunoglobulin into the corresponding variable domains of a human antibody. The mouse framework regions (FR) in the chimeric monoclonal antibody are also replaced with human FR sequences. To preserve the stability and antigen specificity of the humanized monoclonal, one or more human FR residues may be replaced by the mouse counterpart residues. Humanized monoclonal antibodies may be used for therapeutic treatment of subjects. Techniques for production of humanized monoclonal antibodies are well known in the art. (See, e.g., Jones et al., 1986, Nature, 321:522; Riechmann et al., Nature, 1988, 332:323; Verhoeyen et al., 1988, Science, 239:1534; Carter et al., 1992, Proc. Nat'l Acad. Sci. USA, 89:4285; Sandhu, Crit. Rev. Biotech., 1992, 12:437; Tempest et al., 1991, Biotechnology 9:266; Singer et al., J. Immun., 1993, 150:2844.

In another aspect, the invention provides a pharmaceutical composition comprising Dsg2 monoclonal antibody or an antigen-binding portion thereof of the invention and a pharmaceutically acceptable carrier or excipient. Pharmaceutically acceptable carriers comprising excipients and auxiliaries that are well known in the art and are relatively inert substances that facilitate administration of the antibody or which aid processing of the active compounds into preparations that are pharmaceutically optimized for delivery to the site of action. Suitable excipients or additives include, but are not limited to, stabilizing agents, wetting and emulsifying agents, salts for varying osmolarity, encapsulating agents, buffers, and skin penetration enhancers. In certain preferred embodiments the pharmaceutical compositions may be provided in a lyophilized form and reconstituted in, for example, buffered saline prior to administration.

Disclosed antibodies for systemic administration may be formulated for enteral, parenteral or topical administration. Indeed, all three types of formulation may be used simultaneously to achieve systemic administration of the active ingredient. Excipients as well as formulations for parenteral and nonparenteral drug delivery are set forth in Remington, The Science and Practice of Pharmacy 20th Ed. Mack Publishing (2000). Suitable formulations for parenteral administration include aqueous solutions of the active compounds in water-soluble form, for example, water-soluble salts. In addition, suspensions of the active compounds as appropriate for oily injection suspensions may be administered. Suitable lipophilic solvents or vehicles include fatty oils, for example, hexylsubstituted poly(lactide), sesame oil, or synthetic fatty acid esters, for example, ethyl oleate or triglycerides. Aqueous injection suspensions may contain substances that increase the viscosity of the suspension and include, for example, sodium carboxymethyl cellulose, sorbitol, and/or dextran. Optionally, the suspension may also contain stabilizers. Liposomes can also be used to encapsulate the agent for delivery into the cell.

Suitable formulations for enteral administration include hard or soft gelatin capsules, pills, tablets, including coated tablets, elixirs, suspensions, syrups or inhalations and controlled release forms thereof.

In general, the compounds and compositions of the invention, comprising Dsg2 monoclonal antibody may be administered in vivo, to a subject in need thereof, by various routes, including, but not limited to, oral, intravenous, intra-arterial, subcutaneous, parenteral, intranasal, intramuscular, intracranial, intracardiac, intraventricular, intratracheal, buccal, rectal, intraperitoneal, intradermal, topical, transdermal, and intrathecal, or otherwise by implantation or inhalation. The subject compositions may be formulated into preparations in solid, semi-solid, liquid, or gaseous forms; including, but not limited to, tablets, capsules, powders, granules, ointments, solutions, suppositories, enemas, injections, inhalants, and aerosols. The appropriate formulation and route of administration may be selected according to the intended application and therapeutic regimen.

In one aspect, the invention provides a method for treating angiogenesis, comprising administering a monoclonal antibody of the invention to a subject.

In one embodiment, the invention provides a method for treating cancer and/or inhibiting invasion and metastasis, comprising administering a monoclonal antibody of the invention to a subject. In one embodiment, the method can reduce EMT and the cell metastasis and/or cell invasion promoting function of Dsg2. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, melanoma, esophageal cancer, lung cancer and the like. Preferably, the cancer is renal cancer, melanoma, lung cancer, esophageal cancer, cervical cancer, breast cancer or pancreatic cancer.

The particular dosage regimen, i.e., dose, timing and repetition, will depend on the particular individual and that individual's medical history, as well as empirical considerations such as pharmacokinetics (e.g., half-life, clearance rate, etc.). Frequency of administration may be determined and adjusted over the course of therapy, and is based on reducing the number of proliferative or tumorigenic cells, maintaining the reduction of such neoplastic cells, reducing the proliferation of neoplastic cells, or delaying the development of metastasis. In other embodiments the dosage administered may be adjusted or attenuated to manage potential side effects and/or toxicity. Alternatively, sustained continuous release formulations of a subject therapeutic composition may be appropriate. In general, the antibodies of the invention may be administered in various ranges. These include about 100 ug/kg body weight to about 100 mg/kg body weight per dose; preferably, about 100 ug/kg to about 1 mg/kg, about 100 ug/kg to about 500 ug/kg, about 500 ug/kg to about 1 mg/kg, about 1 mg/kg, about 1 mg/kg to about 100 mg/kg, 10 mg/kg to about 100 mg/kg, 50 mg/kg to about 100 mg/kg, 10 mg/kg to about 50 mg/kg body weight per dose.

Combination therapies may be particularly useful in decreasing or inhibiting unwanted neoplastic cell proliferation, decreasing the occurrence of cancer, decreasing or preventing the recurrence of cancer, or decreasing or preventing the spread or metastasis of cancer. That is, the disclosed antibodies may, in certain embodiments provide an enhanced effect that potentiates the mode of action of another administered therapeutic agent. In the context of the instant invention "combination therapy" shall be interpreted broadly and merely refers to the administration of an antibody and one or more anti-cancer agents that include, but are not limited to, cytotoxic agents, cytostatic agents, anti-angiogenic agents, chemotherapeutic agents, radiotherapy and radiotherapeutic agents, targeted anti-cancer agents (including both monoclonal antibodies and small molecule entities), therapeutic antibodies, cancer vaccines, cytokines, hormone therapies, radiation therapy and anti-metastatic agents and immunotherapeutic agents, including both specific and non-specific approaches.

The combination therapy may be administered once, twice or at least for a period of time until the condition is treated, palliated or cured. In some embodiments, the combination therapy is administered multiple times, for example, from three times daily to once every six months. The administering may be on a schedule such as three times daily, twice daily, once daily, once every two days, once every three days, once weekly, once every two weeks, once every month, once every two months, once every three months, once every six months or may be administered continuously. The combination therapy may be administered via any route, as noted previously. The combination therapy may be administered at a site distant from the site of the tumor.

In one embodiment an antibody is administered in combination with one or more anti-cancer agents for a short treatment cycle to a subject in need thereof. The invention also contemplates discontinuous administration or daily doses divided into several partial administrations. The antibody and anti-cancer agent may be administered interchangeably, on alternate days or weeks; or a sequence of antibody treatments may be given, followed by one or more treatments of anti-cancer agent therapy. In any event, as will be understood by those of ordinary skill in the art, the appropriate doses of chemotherapeutic agents will be generally around those already employed in clinical therapies wherein the chemotherapeutics are administered alone or in combination with other chemotherapeutics.

In another preferred embodiment the antibodies of the instant invention may be used in maintenance therapy to reduce or eliminate the chance of tumor recurrence following the initial presentation of the disease.

EXAMPLES

Example 1 Preparation of mAbs Against to Human Desmoglein2 (Dsg2)

Hybridoma methodology was employed for the development of mAbs specific to Dsg2. The antigen used for immunizing BALB/c mice was a recombinant fusion protein containing the Dsg2 extracellular domain 2.

Briefly, the coding sequence of a truncated Dsg2, amplified from the plasmid IMAGE 8694 (encoding the full-length human Dsg2), was cloned into pET-28a vector (Novagen). The Dsg2-EC2 construct contains an N-terminal and an C-terminal hexahistidine-tags for purification and was expressed in the *E. coli* strain BL21.

To induce anti-Dsg2 immune response, BALB/c mice were immunized twice subcutaneously with 50 µg of Dsg2 EC2 recombinant proteins that were emulsified in TiterMax Gold adjuvant (Sigma-Aldrich) according manufacturer's suggestions at 2 week intervals. A final boost was given intraperitoneally with 0.1 mg of Dsg2 EC2 recombinant proteins without adjuvant. One day before fusion, NS0 cells were reseeded in fresh DMEM medium (Invitrogen) supplemented with 10% heat-inactivated fetal bovine serum (FBS; Invitrogen), and 1% penicillin-streptomycin mixture (100× Pen-Strep solution; Invitrogen) at a cell density of $5 \times 10^5$ cells/ml. Three days after the final boost, the spleen cells from two immunized mice were harvested and washed with serum-free DMEM medium twice. $5 \times 10^7$ NS0 cells were harvested and washed with serum-free DMEM medium twice. After washing, spleen cells and NS0 cells were fused by adding 1 ml of pre-warmed 50% polyethyleneglycerol 1500 (PEG 1500, Roche Applied Science) while continually stirring cells gently with the pipette tip over 1 min, stirring cells for further 1 min, adding 2 ml pre-warmed serum-free DMEM over 2 min, and finally adding 8 ml serum-free DMEM over 2 min. After centrifugation at 200×g for 10 min, fused cells were resuspended with 600 ml of HAT medium [DMEM medium supplemented with 2% hypoxanthine-aminopterin-thymidine mixture (50×HAT solution; Invitrogen), 10% BM-Condimed H1 (Roche Applied Science), 10% heat-inactivated FBS, and 1% penicillin-streptomycin mixture] and distributed into 30 96-well culture plates at 200 µl/well. On days 3, 100 µl of HAT medium was added to each well. On days 7 and 10, medium was freshened by aspirating half the volume of each well and replacing with HAT medium. On days 14, hybridoma supernatants were used to screen anti-Dsg2 mAbs for binding to Dsg2 EC2 proteins by enzyme-linked immunosorbent assay (ELISA).

Hybridoma cells secreting antibodies with the desired antigen-binding activities were screened as follows. Microtiter plates were coated by incubating with 1 µg/mL of Dsg2 EC2 and various other control proteins or 10 µg/mL of various peptides in carbonate buffer, 0.1M, pH 9.6, overnight at 4° C. The wells were blocked with 1% BSA in PBS, pH=7.3 for 1 hour and incubated with the antisera or control antibodies at various dilutions for 1 hour at 37° C. After washing, the ligand-bound antibodies were detected by HRP-conjugated goat anti-mouse IgG, Fcγ fragment specific (Jackson ImmunoResearch) at 1:10,000 and incubated for 1 hour at 37° C., followed by incubation with TMB substrate (Clinical Scientific Products). The OD was determined at 450 nm. A number of positive clones, including mAb 3D4 and 13D3, were selected for further characterization.

Figure 2:
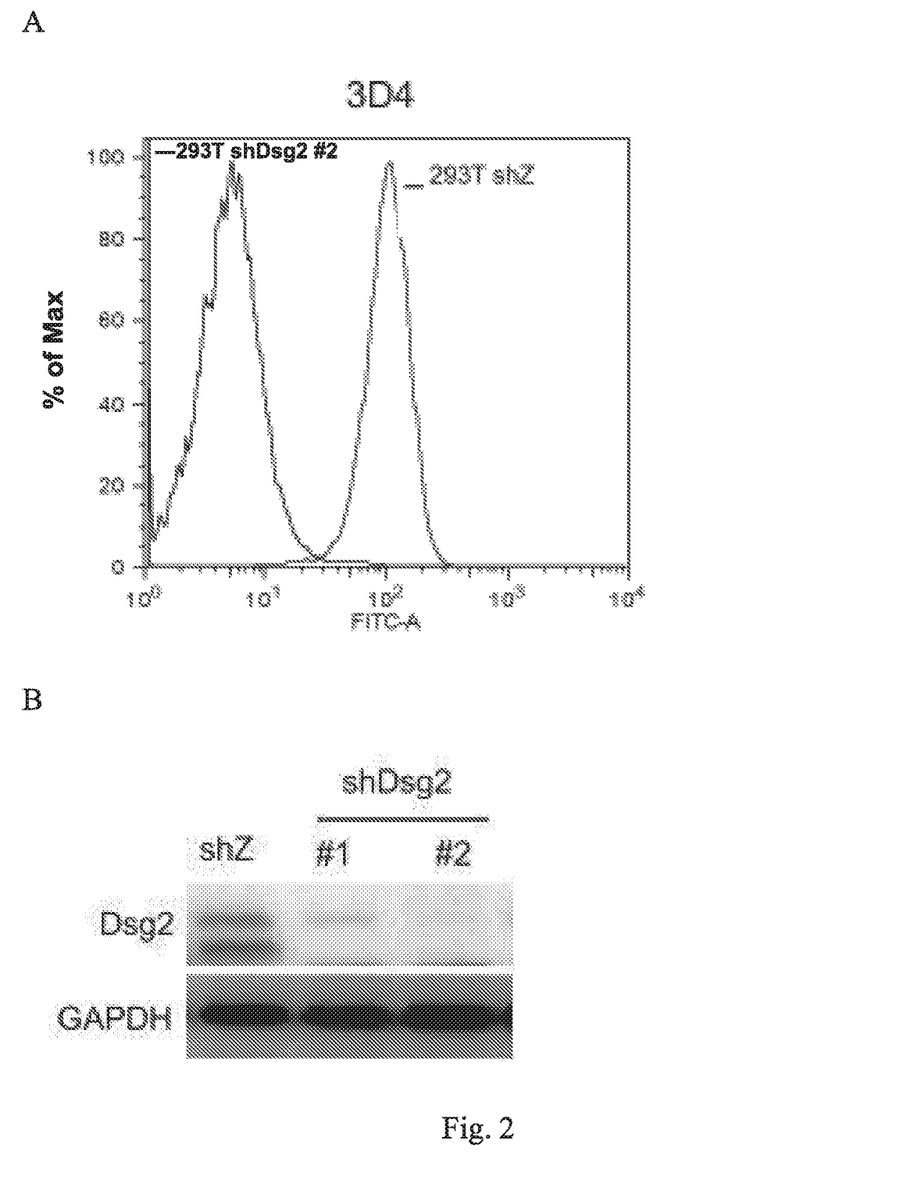
Figure 3:
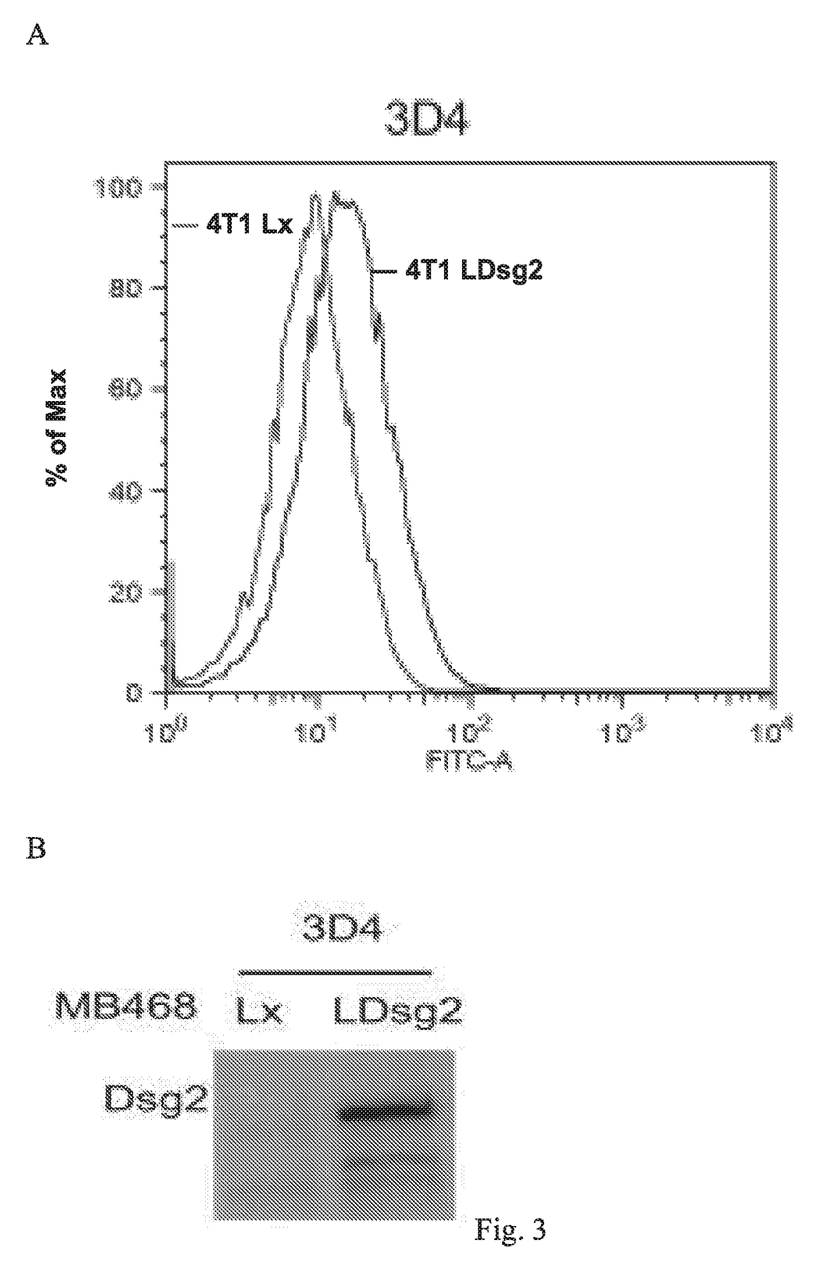

The further characterization studies by flow cytometric analysis and Western blotting, as shown in FIG. 2 (Dsg2 knock down) and FIG. 3 (Dsg2 over-expression), display that both 3D4 and 13D3 can specifically bind to Dsg2-expressing cells.

Figure 1:
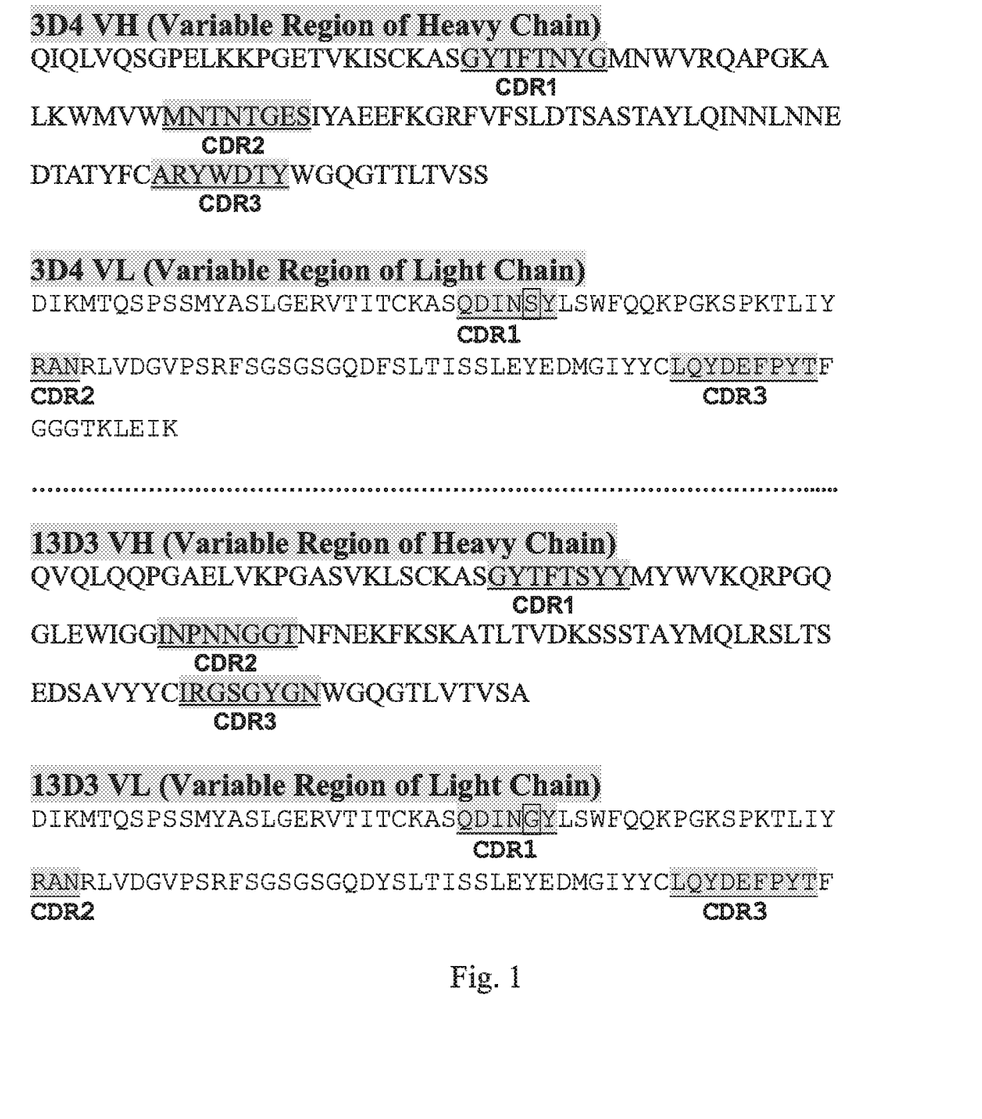
FIG. 1 shows VH and VL sequences of mAb 3D4 and mAb 13D3.

The VH and VL gene segments of the above noted antibody clones were amplified by PCR from the hybridoma clones secreting the antibody. The gene segments thus obtained were sequenced to determine the VH and VL sequences of mAb 3D4 and mAb 13D3, which are shown in FIG. 1. The complementarity determining regions of the VH and VL regions are underlined, and their sequences are also shown in FIG. 1.

Example 2 the Binding of Dsg2 mAbs 3D4 and 13D3 to Various Kinds of Human Cancer Cells Mouse colon cancer cell line CT26, canine kidney cell line MDCK, human melanoma cell line A375.S2, human lung cancer cell line A549, human esophageal cancer cell line BE3, human cervical cancer cell line HeLa, human breast cancer cell line MDA-MB-231, and human pancreatic cancer cell line PANC-1 were cultured and used to study the binding activities of Dsg2 mAb 3D4 and 13D3.

Figure 4:
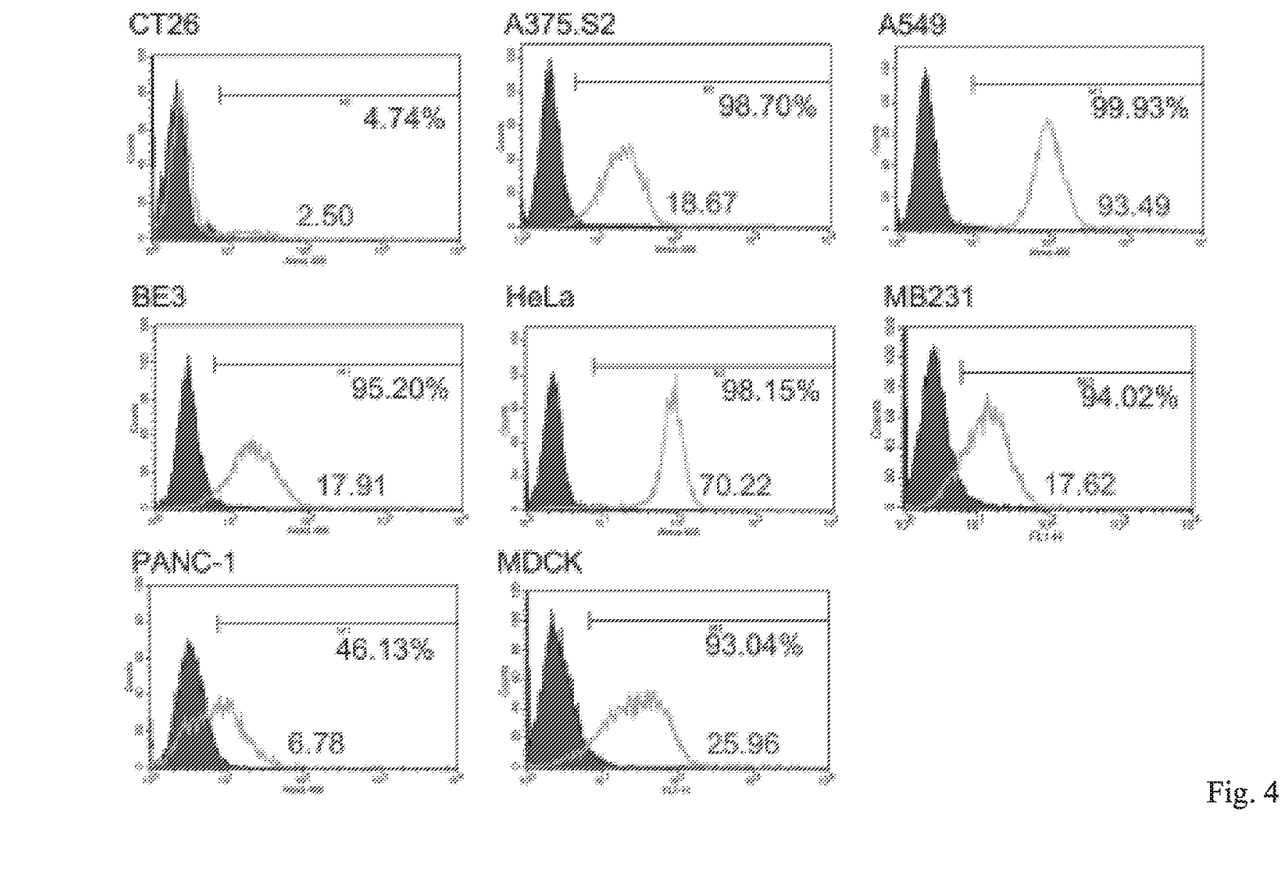
FIG. 4 shows Dsg2 mAbs 3D4 recognize different kinds of epithelial-derived human cancer cells.
Figure 5:
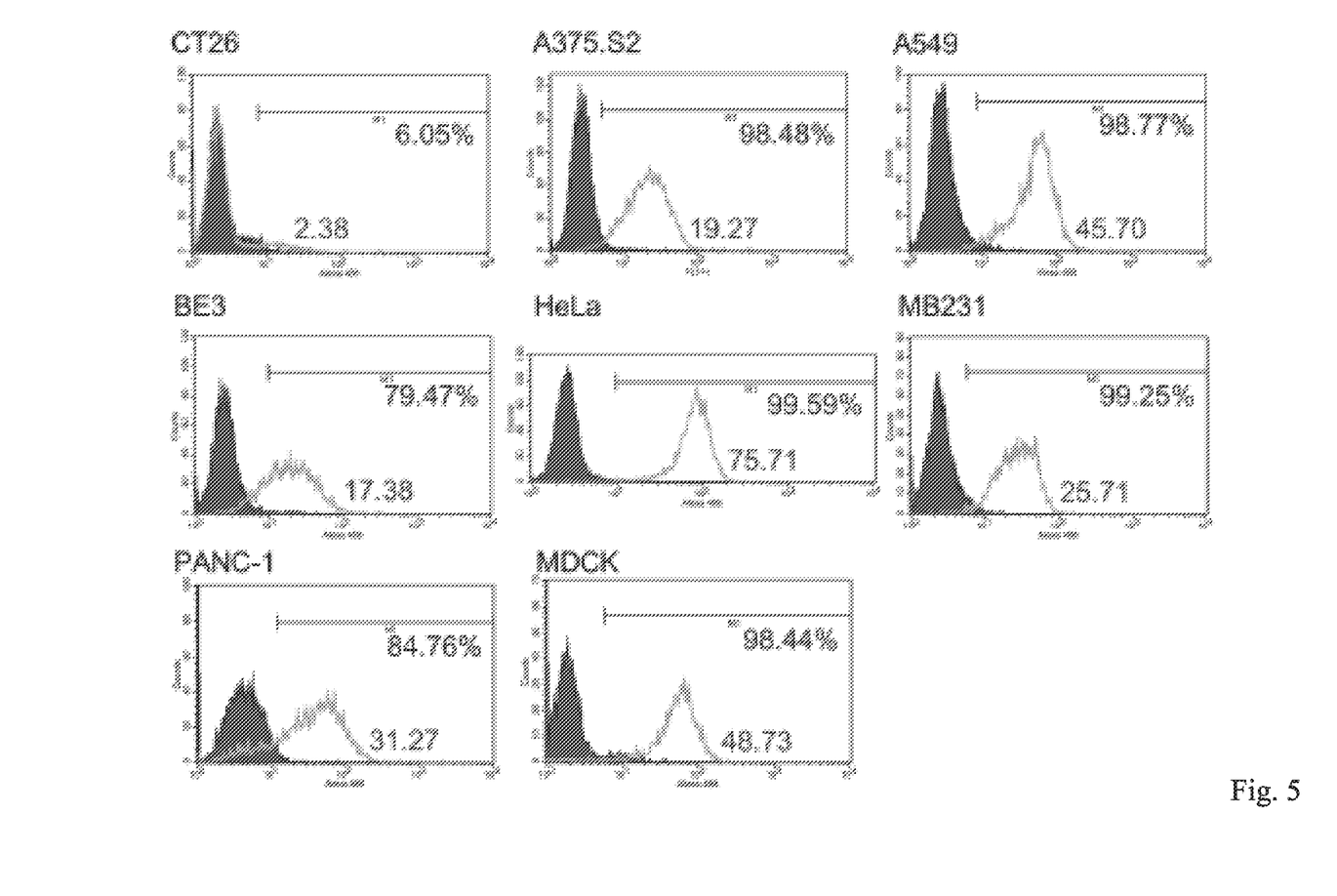
FIG. 5 shows Dsg2 mAbs 13D3 recognize different kinds of epithelial-derived human cancer cells.

These cells were incubated with mAb 3D4 at 10 µg/ml or mAb 13D3 at 10 µg/ml on ice for 20 minutes and then subjected to flow cytometric analysis. The results obtained from these studies, as shown in FIG. 4 and FIG. 5, indicate that both 3D4 and 13D3 can bind to various kinds of human cancer cells.

We claim:

1. A Dsg2 monoclonal antibody or an antigen-binding portion thereof comprising
   a) heavy chain complementarity determining region 1 (H-CDR1) of SEQ ID NO:1, a heavy chain CDR2 (H-CDR2) of SEQ ID NO:3, a heavy chain CDR3 (H-CDR3) of SEQ ID NO:5 and a light chain CDR1 (L-CDR1) of SEQ ID NO:7, a light chain CDR2 (L-CDR2) of SEQ ID NO:9, and a light chain CDR3 (L-CDR3) of SEQ ID NO:10, or
   b) H-CDR1 of SEQ ID NO:2, H-CDR2 of SEQ ID NO:4, H-CDR3 of SEQ ID NO:6, and L-CDR1 of SEQ ID NO:8, L-CDR2 of SEQ ID NO:9, and L-CDR3 of SEQ ID NO:10.

2. The Dsg2 monoclonal antibody or an antigen-binding portion thereof of claim 1, wherein the Dsg2 monoclonal antibody or an antigen-binding portion thereof comprises H-CDR1 of SEQ ID NO:1, H-CDR2 of SEQ ID NO:3 and H-CDR3 of SEQ ID NO:5; L-CDR1 of SEQ ID NO:7, L-CDR2 of SEQ ID NO:9 and L-CDR3 of SEQ ID NO:10.

3. The Dsg2 monoclonal antibody or an antigen-binding portion thereof of claim 1, wherein the Dsg2 monoclonal antibody or an antigen-binding portion thereof comprises H-CDR1 of SEQ ID NO:2, H-CDR2 of SEQ ID NO:4, H-CDR3 of SEQ ID NO:6; L-CDR1 of SEQ ID NO:8, L-CDR2 of SEQ ID NO:9, and L-CDR3 of SEQ ID NO:10.

4. The Dsg2 monoclonal antibody or an antigen-binding portion thereof of claim 1, wherein the Dsg2 monoclonal antibody or an antigen-binding portion thereof comprises a light chain variable region amino acid sequence of SEQ ID NO:11 and a heavy chain variable region amino acid sequence of SEQ ID NO:13.

5. The Dsg2 monoclonal antibody or an antigen-binding portion thereof of claim 1, wherein the Dsg2 monoclonal antibody or an antigen-binding portion thereof comprises a light chain variable region amino acid sequence of SEQ ID NO:12 and a heavy chain variable region amino acid sequence of SEQ ID NO:14.

6. A pharmaceutical composition comprising the Dsg2 monoclonal antibody or an antigen-binding portion thereof of claim 1 and a pharmaceutically acceptable carrier or excipient.

* * * * *

SEQUENCE LISTING

```
<160> NUMBER OF SEQ ID NOS: 14

<210> SEQ ID NO 1
<211> LENGTH: 8
<212> TYPE: PRT
<213> ORGANISM: Artificial
<220> FEATURE:
<223> OTHER INFORMATION: H-CDR1

<400> SEQUENCE: 1

Gly Tyr Thr Phe Thr Asn Tyr Gly
1               5

<210> SEQ ID NO 2
<211> LENGTH: 8
<212> TYPE: PRT
<213> ORGANISM: Artificial
<220> FEATURE:
<223> OTHER INFORMATION: H-CDR1
```

```
<400> SEQUENCE: 2

Gly Tyr Thr Phe Thr Ser Tyr Tyr
1               5

<210> SEQ ID NO 3
<211> LENGTH: 8
<212> TYPE: PRT
<213> ORGANISM: Artificial
<220> FEATURE:
<223> OTHER INFORMATION: H-CDR2

<400> SEQUENCE: 3

Met Asn Thr Asn Thr Gly Glu Ser
1               5

<210> SEQ ID NO 4
<211> LENGTH: 8
<212> TYPE: PRT
<213> ORGANISM: Artificial
<220> FEATURE:
<223> OTHER INFORMATION: H-CDR2

<400> SEQUENCE: 4

Ile Asn Pro Asn Asn Gly Gly Thr
1               5

<210> SEQ ID NO 5
<211> LENGTH: 7
<212> TYPE: PRT
<213> ORGANISM: Artificial
<220> FEATURE:
<223> OTHER INFORMATION: H-CDR3

<400> SEQUENCE: 5

Ala Arg Tyr Trp Asp Thr Tyr
1               5

<210> SEQ ID NO 6
<211> LENGTH: 8
<212> TYPE: PRT
<213> ORGANISM: Artificial
<220> FEATURE:
<223> OTHER INFORMATION: H-CDR3

<400> SEQUENCE: 6

Ile Arg Gly Ser Gly Tyr Gly Asn
1               5

<210> SEQ ID NO 7
<211> LENGTH: 6
<212> TYPE: PRT
<213> ORGANISM: Artificial
<220> FEATURE:
<223> OTHER INFORMATION: L-CDR1

<400> SEQUENCE: 7

Gln Asp Ile Asn Ser Tyr
1               5

<210> SEQ ID NO 8
<211> LENGTH: 6
<212> TYPE: PRT
<213> ORGANISM: Artificial
<220> FEATURE:
<223> OTHER INFORMATION: L-CDR1

<400> SEQUENCE: 8
```

```
Gln Asp Ile Asn Gly Tyr
1               5
```

<210> SEQ ID NO 9
<211> LENGTH: 3
<212> TYPE: PRT
<213> ORGANISM: Artificial
<220> FEATURE:
<223> OTHER INFORMATION: L-CDR2

<400> SEQUENCE: 9

```
Arg Ala Asn
1
```

<210> SEQ ID NO 10
<211> LENGTH: 9
<212> TYPE: PRT
<213> ORGANISM: Artificial
<220> FEATURE:
<223> OTHER INFORMATION: L-CDR3

<400> SEQUENCE: 10

```
Leu Gln Tyr Asp Glu Phe Pro Tyr Thr
1               5
```

<210> SEQ ID NO 11
<211> LENGTH: 107
<212> TYPE: PRT
<213> ORGANISM: Artificial
<220> FEATURE:
<223> OTHER INFORMATION: 3D4 VL (Variable Region of Light Chain)

<400> SEQUENCE: 11

```
Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
50                  55                  60

Ser Gly Ser Gly Gln Asp Phe Ser Leu Thr Ile Ser Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Ile Lys
            100                 105
```

<210> SEQ ID NO 12
<211> LENGTH: 107
<212> TYPE: PRT
<213> ORGANISM: Artificial
<220> FEATURE:
<223> OTHER INFORMATION: 13D3 VL (Variable Region of Light Chain)

<400> SEQUENCE: 12

```
Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Gly Tyr
            20                  25                  30

Leu Ser Trp Phe Gln Gln Lys Pro Gly Lys Ser Pro Lys Thr Leu Ile
        35                  40                  45
```

```
Tyr Arg Ala Asn Arg Leu Val Asp Gly Val Pro Ser Arg Phe Ser Gly
        50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Ile Lys
            100                 105

<210> SEQ ID NO 13
<211> LENGTH: 114
<212> TYPE: PRT
<213> ORGANISM: Artificial
<220> FEATURE:
<223> OTHER INFORMATION: 3D4 VH (Variable Region of Heavy Chain)

<400> SEQUENCE: 13

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
                20                  25                  30

Gly Met Asn Trp Val Arg Gln Ala Pro Gly Lys Ala Leu Lys Trp Met
            35                  40                  45

Val Trp Met Asn Thr Asn Thr Gly Glu Ser Ile Tyr Ala Glu Glu Phe
        50                  55                  60

Lys Gly Arg Phe Val Phe Ser Leu Asp Thr Ser Ala Ser Thr Ala Tyr
65                  70                  75                  80

Leu Gln Ile Asn Asn Leu Asn Asn Glu Asp Thr Ala Thr Tyr Phe Cys
                85                  90                  95

Ala Arg Tyr Trp Asp Thr Tyr Trp Gly Gln Gly Thr Ser Leu Thr Val
            100                 105                 110

Ser Ser

<210> SEQ ID NO 14
<211> LENGTH: 115
<212> TYPE: PRT
<213> ORGANISM: Artificial
<220> FEATURE:
<223> OTHER INFORMATION: 13D3 VH (Variable Region of Heavy Chain)

<400> SEQUENCE: 14

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
                20                  25                  30

Tyr Met Tyr Trp Val Lys Gln Arg Pro Gly Gln Gly Leu Glu Trp Ile
            35                  40                  45

Gly Gly Ile Asn Pro Asn Asn Gly Gly Thr Asn Phe Asn Glu Lys Phe
        50                  55                  60

Lys Ser Lys Ala Thr Leu Thr Val Asp Lys Ser Ser Ser Thr Ala Tyr
65                  70                  75                  80

Met Gln Leu Arg Ser Leu Thr Ser Glu Asp Ser Ala Val Tyr Tyr Cys
                85                  90                  95
```

```
Ile Arg Gly Ser Gly Tyr Gly Asn Trp Gly Gln Gly Thr Leu Val Thr
            100                 105                 110
Val Ser Ala
    115
```